US009626478B2

(12) United States Patent
Armstrong

(10) Patent No.: US 9,626,478 B2
(45) Date of Patent: Apr. 18, 2017

(54) SYSTEM AND METHOD FOR TRACKING BIOLOGICAL AGE OVER TIME BASED UPON HEART RATE VARIABILITY

(71) Applicant: LOGITECH EUROPE, S.A., Lausanne (CH)

(72) Inventor: Judd Armstrong, Parrearra (AU)

(73) Assignee: LOGITECH EUROPE, S.A., Lausanne (CH)

(*) Notice: Subject to any disclaimer, the term of this patent is extended or adjusted under 35 U.S.C. 154(b) by 291 days.

(21) Appl. No.: 14/244,464

(22) Filed: Apr. 3, 2014

(65) Prior Publication Data

US 2015/0120202 A1   Apr. 30, 2015

Related U.S. Application Data

(63) Continuation-in-part of application No. 14/137,734, filed on Dec. 20, 2013, which is a continuation-in-part of application No. 14/062,815, filed on Oct. 24, 2013.

(51) Int. Cl.
*A61B 5/00* (2006.01)
*G06F 19/00* (2011.01)
*A61B 5/024* (2006.01)
*A61B 5/11* (2006.01)

(52) U.S. Cl.
CPC ........ *G06F 19/322* (2013.01); *A61B 5/02405* (2013.01); *A61B 5/1118* (2013.01); *A61B 5/4821* (2013.01); *A61B 5/681* (2013.01); *A61B 5/72* (2013.01); *A61B 5/7275* (2013.01); *A61B 5/74* (2013.01); *G06F 19/3431* (2013.01); *A61B 2503/12* (2013.01)

(58) Field of Classification Search
None
See application file for complete search history.

(56) References Cited

U.S. PATENT DOCUMENTS

| | | |
|---|---|---|
| 2,189,096 A | 2/1940 | Alonge |
| 3,543,724 A | 12/1970 | Kirkpatrick et al. |
| 3,978,849 A | 9/1976 | Geneen |
| 4,129,124 A | 12/1978 | Thalmann |
| 4,224,948 A | 9/1980 | Cramer et al. |
| 4,307,727 A | 12/1981 | Haynes |
| 4,331,154 A | 5/1982 | Broadwater et al. |
| 4,407,295 A | 10/1983 | Steuer et al. |
| 4,409,983 A | 10/1983 | Albert |

(Continued)

OTHER PUBLICATIONS

Office Action dated Feb. 22, 2016 for U.S. Appl. No. 14/137,942.
Office Action dated May 11, 2016 for U.S. Appl. No. 14/140,414.

*Primary Examiner* — William Thomson
*Assistant Examiner* — Marie Archer
(74) *Attorney, Agent, or Firm* — Patterson & Sheridan, LLP

(57) ABSTRACT

A system and method for tracking biological age over time based upon heart rate variability includes an activity monitoring device configured to measure and transmit one or more biological age parameters, including heart rate variability, to a biological age calculation and display module configured to calculate a biological age factor as a function of the biological age parameters, calculate biological age as a function of the biological age factor and the user's actual age, and display the biological age.

22 Claims, 6 Drawing Sheets

(56) References Cited

U.S. PATENT DOCUMENTS

| | | | |
|---|---|---|---|
| 4,491,970 A | 1/1985 | Lawhite et al. |
| 5,301,154 A | 4/1994 | Suga |
| 5,392,261 A | 2/1995 | Hsu |
| 5,406,952 A | 4/1995 | Barnes et al. |
| 5,524,637 A | 6/1996 | Erickson |
| 5,734,625 A | 3/1998 | Kondo |
| 5,755,623 A | 5/1998 | Mizenko |
| 5,890,128 A | 3/1999 | Diaz et al. |
| 5,899,370 A | 5/1999 | Bould |
| 6,104,947 A | 8/2000 | Heikkila et al. |
| 6,151,968 A | 11/2000 | Chou |
| 6,269,339 B1 * | 7/2001 | Silver | G06F 19/3456 600/300 |
| 6,361,503 B1 | 3/2002 | Starobin et al. |
| 6,516,222 B2 | 2/2003 | Fukuda |
| 6,554,776 B1 | 4/2003 | Snow et al. |
| 6,736,759 B1 | 5/2004 | Stubbs et al. |
| 7,192,401 B2 | 3/2007 | Saalasti et al. |
| 7,717,827 B2 | 5/2010 | Kurunmaki et al. |
| 7,914,425 B2 | 3/2011 | Hanoun |
| 8,812,428 B2 | 8/2014 | Mollicone et al. |
| 8,992,385 B2 | 3/2015 | Lemos |
| 2002/0151811 A1 | 10/2002 | Starobin et al. |
| 2002/0188210 A1 | 12/2002 | Aizawa |
| 2003/0013995 A1 | 1/2003 | Oshima et al. |
| 2003/0065269 A1 | 4/2003 | Vetter et al. |
| 2005/0056655 A1 | 3/2005 | Gary |
| 2005/0116811 A1 | 6/2005 | Eros et al. |
| 2005/0228239 A1 * | 10/2005 | Shallenberger | A61K 31/56 600/300 |
| 2005/0256416 A1 | 11/2005 | Chen |
| 2006/0183980 A1 | 8/2006 | Yang |
| 2007/0118043 A1 | 5/2007 | Oliver et al. |
| 2008/0132383 A1 | 6/2008 | Einav et al. |
| 2008/0228089 A1 | 9/2008 | Cho et al. |
| 2009/0312656 A1 | 12/2009 | Lau et al. |
| 2010/0197463 A1 | 8/2010 | Haughay, Jr. et al. |
| 2011/0021319 A1 | 1/2011 | Nissila et al. |
| 2011/0092790 A1 | 4/2011 | Wilder-Smith et al. |
| 2011/0190645 A1 | 8/2011 | Hunt et al. |
| 2011/0260870 A1 | 10/2011 | Bailey |
| 2012/0022341 A1 | 1/2012 | Zdeblick |
| 2012/0168471 A1 | 7/2012 | Wilson |
| 2012/0253485 A1 | 10/2012 | Weast et al. |
| 2013/0018592 A1 | 1/2013 | Mollicone et al. |
| 2013/0064049 A1 | 3/2013 | Pileri et al. |
| 2013/0158423 A1 * | 6/2013 | Kapoor | A61B 5/0432 600/523 |
| 2013/0237778 A1 | 9/2013 | Rouquette |
| 2013/0325396 A1 * | 12/2013 | Yuen | G01C 22/006 702/160 |
| 2014/0005575 A1 * | 1/2014 | Ogawa | A61B 5/1118 600/595 |
| 2014/0032234 A1 | 1/2014 | Anderson |
| 2014/0073486 A1 | 3/2014 | Ahmed et al. |
| 2014/0107493 A1 | 4/2014 | Yuen et al. |
| 2014/0228175 A1 | 8/2014 | Lemos et al. |
| 2014/0270375 A1 | 9/2014 | Canavan et al. |

* cited by examiner

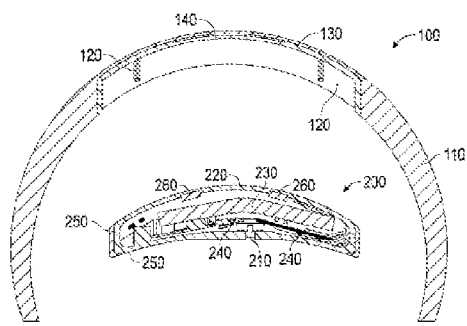
FIG. 1
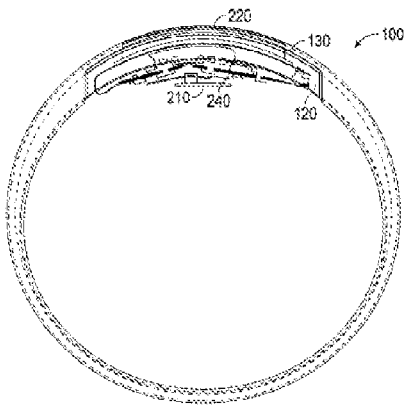
FIG. 3
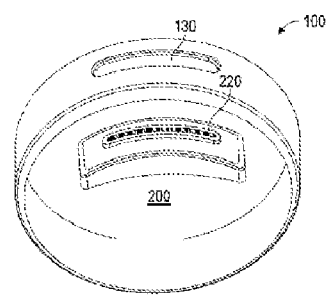
FIG. 2
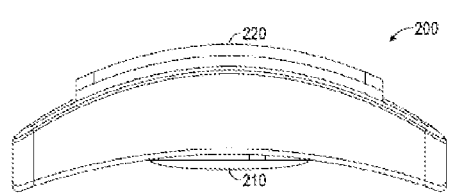
FIG. 4
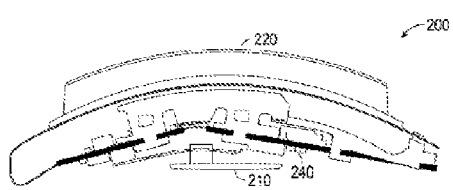
FIG. 5
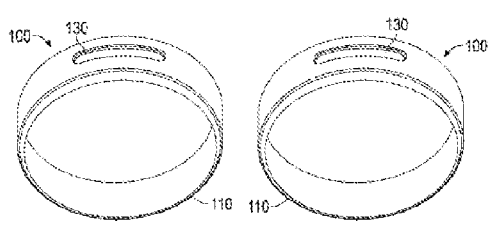
FIG. 6
Figs. 1-6

SYSTEM AND METHOD FOR TRACKING BIOLOGICAL AGE OVER TIME BASED UPON HEART RATE VARIABILITY

CROSS-REFERENCE TO RELATED APPLICATIONS

This application is a continuation-in-part of and claims the benefit of U.S. patent application Ser. No. 14/137,734, filed Dec. 20, 2013, titled "System and Method for Providing a Smart Activity Score," which is a continuation-in-part of U.S. patent application Ser. No. 14/062,815, filed Oct. 24, 2013, titled "Wristband with Removable Activity Monitoring Device." The contents of both the Ser. No. 14/137,734 application and the Ser. No. 14/062,815 application are incorporated herein by reference.

TECHNICAL FIELD

The present disclosure relates generally to fitness monitoring devices, and more particularly to a system and method for tracking biological age over time.

BACKGROUND

Previous generation movement monitoring and fitness tracking devices generally enabled only a tracking of activity that accounts for total calories burned. One issue with currently available fitness tracking devices is that they do not account for the performance state of the user in a scientific, user-specific way. Another issue is that currently available solutions do not account in a precise manner for the health and performance benefits of sustained activity.

Additionally, understanding the effects of physical activity on biological age is becoming more important to many health conscious consumers. Biological age is essentially a person's actual age weighted by factors effecting that person's longevity. For example, factors such as gender, ethnicity, health, eating habits, stress levels, sleep habits, and exercise habits may increase or decrease a person's life expectancy. Biological age may change over time based on changes to any of these factors. Currently available technologies typically only measure biological age based on user input, and are not capable of tracking or monitoring biological age over time based on both user input and measured parameters. In particular, heart rate variability is a measurable parameter and is known to correlate to physiological resilience and behavioral flexibility, which are both important factors in determining biological age. However, currently available technologies do not leverage heart rate variability measurements, or other biological age determining factors measurable by activity monitoring devices, that could be used to semi-automate biological age tracking.

In view of these drawbacks, there exists a long-felt need for fitness monitoring devices capable of combining user input with measured factors, including heart rate variability, to display and track changes in biological age over time.

BRIEF SUMMARY OF THE DISCLOSURE

The present disclosure is directed towards activity monitoring devices. In particular, embodiments of the present invention are directed towards a system and method for tracking biological age over time.

One embodiment of the disclosure provides a method for calculating and tracking biological age over time that includes receiving both user determinable and system measurable biological age parameters, calculating biological age at any given time as a function of these parameters, and displaying the biological age for a given time interval, or as a trend over several intervals. User determinable biological age factors may include actual age, gender, eating habits, health metrics such as cholesterol levels and blood pressure, stress level indicators such as job type and personality, sleep patterns, weight, height, and body fat index. System measurable biological age parameters may include factors measured by an activity monitoring device such as heart rate variability and recovery score, sleep patterns, activity patterns, activity scores, and smart activity scores.

In many embodiments of the disclosure, a system for calculating and tracking biological age over time includes an activity monitoring device and a biological age calculation and display module, wherein the biological age calculation and display module is configured to receive both user determinable and system measurable biological age parameters, calculate biological age at any given time as a function of these biological age parameters, and display the biological age for a given time interval, or as a trend over several intervals.

In many examples of the disclosure, the activity monitoring device measures and transmits the system measurable biological age parameters to the biological age calculation and display module. The activity monitoring device may be a wearable activity monitoring device. The activity monitoring device includes a movement monitoring module that monitors a movement to determine a metabolic loading associated with the movement, a heart rate variability module that detects heart rate variability and calculates a recovery score, a metabolic activity score module that creates and updates a metabolic activity score based on the metabolic loading and the movement, and a smart activity score module that creates and updates a smart activity score by modifying, based on the fatigue level, the metabolic activity score. Several examples include systems and methods for comparing biological age with physical activity monitoring, calculating recommended activity regiments to reduce, maintain, or achieve a desired biological age, and monitoring progress towards achieving the desired biological age. In some examples, a system and method for tracking biological age over time also displays physical activity trends over time, and may additionally flag biological age changes in a correlated or combined display with physical activity trend changes such that a user may determine what physical activity characteristics may have caused the change in biological age.

Other features and aspects of the disclosure will become apparent from the following detailed description, taken in conjunction with the accompanying drawings, which illustrate, by way of example, the features in accordance with embodiments of the disclosure. The summary is not intended to limit the scope of the disclosure, which is defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments of the disclosure.

FIG. 1 illustrates a cross-sectional view of the wristband and electronic modules of an example activity monitoring device.

FIG. 2 illustrates a perspective view of an example activity monitoring device.

FIG. 3 illustrates a cross-sectional view of an example assembled activity monitoring device.

FIG. 4 illustrates a side view of an example electronic capsule.

FIG. 5 illustrates a cross-sectional view of an example electronic capsule.

FIG. 6 illustrates perspective views of wristbands as used in one embodiment of the disclosed activity monitoring device.

Figure 7A:
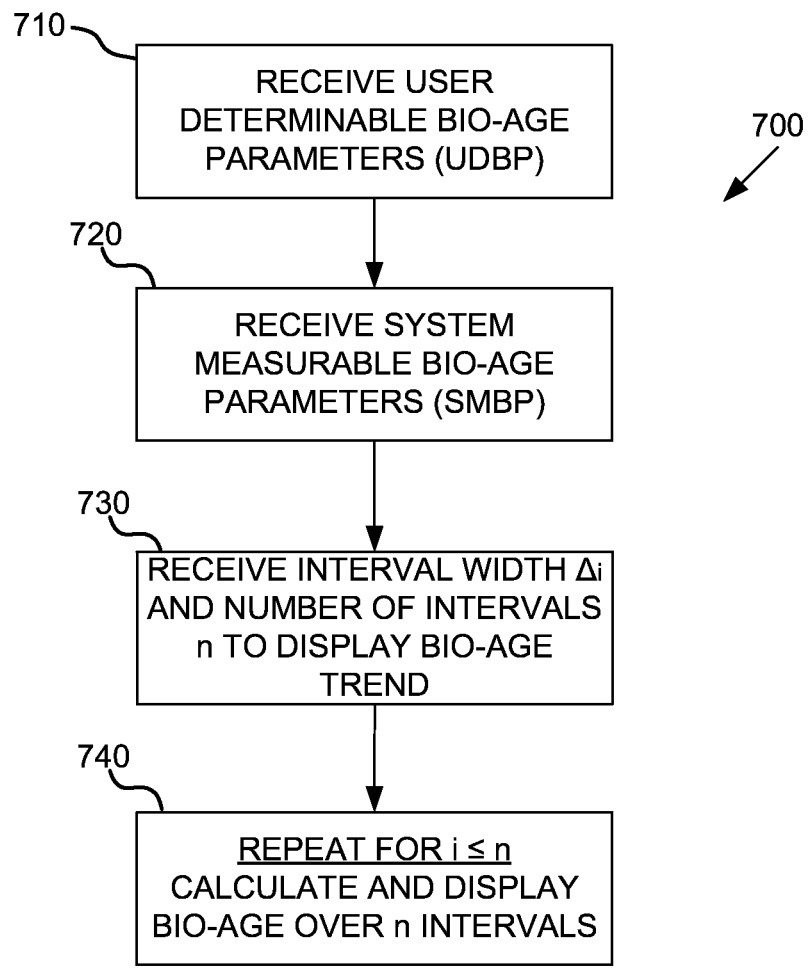
FIG. 7A is a flow diagram illustrating an exemplary method for tracking biological age over time.

The figures are not intended to be exhaustive or to limit the disclosure to the precise form disclosed. It should be understood that the disclosure can be practiced with modification and alteration, and that the disclosure can be limited only by the claims and the equivalents thereof.

DETAILED DESCRIPTION

Embodiments of the present disclosure are directed toward systems and methods for tracking biological age over time based on both user determinable and system measurable parameters.

According to some embodiments of the disclosure, a method for calculating and tracking biological age over time includes receiving user determinable biological age parameters, receiving system measurable biological age parameters, calculating biological age at any given time as a function of user input and system determinable biological age parameters, and displaying the biological age for a given time interval, or as a trend over several intervals. In other embodiments, a system for calculating and tracking biological age over time comprises an activity monitoring device and a biological age calculation and display module, wherein the biological age calculation and display module is configured to receive user determinable biological age parameters, receive system measurable biological age parameters, calculate biological age at any given time as a function of user input and system determinable biological age parameters, and display the biological age for a given time interval, or as a trend over several intervals.

FIG. 1 is a diagram illustrating a cross-sectional view of an exemplary embodiment of an activity monitoring device. Referring now to FIG. 1, an activity monitoring device comprises an electronic capsule 200 and a wristband 100. The electronic capsule 200 comprises a wrist biosensor 210, a finger biosensor 220, a battery 230, one or more logic circuits 240, and a casing 250.

In some embodiments, the logic circuits 240 comprise an accelerometer, a wireless transmitter, and circuitry. The logic circuits may further comprise a gyroscope. These logic circuits may be configured to process electronic input signals from the biosensors and the accelerometer, store the processed signals as data, and output the data using the wireless transmitter. The transmitter is configured to communicate using available wireless communications standards. For example, in some embodiments, the wireless transmitter may be a Bluetooth® transmitter, a Wi-Fi transmitter, a GPS transmitter, a cellular transmitter, or some combination thereof. In an alternative embodiment, the wireless transmitter may further comprise a wired interface (e.g. USB, fiber optic, HDMI, etc.) for communicating stored data.

The logic circuits 240 may be electrically coupled to the wrist biosensor 210 and the finger biosensor 220. In addition, the logic circuits are configured to receive and process a plurality of electric signals from each of the wrist biosensor 210 and finger biosensor 220. In some embodiments, the plurality of electric signals comprise an activation time signal and a recovery time signal such that the logic circuits 240 may process the plurality of signals to calculate an activation recovery interval equal to the difference between the activation time signal and the recovery time signal. In some embodiments, the plurality of signals may comprise electro-cardio signals from a heart, and the logic circuits may process the electro-cardio signals to calculate and store a RR-interval, and the RR-interval may be used to calculate and store a heart rate variability (HRV) value. Here, the RR-interval is equal to the delta in time between two R-waves, where the R-waves are the electro-cardio signals generated by a ventricle contraction in the heart.

In some embodiments, the logic circuits may further detect and store metrics such as the amount of physical activity, sleep, or rest over a recent time period, or the amount of time without physical activity over a recent period of time. The logic circuits may then use the HRV, or the HRV in combination with said metrics, to calculate a recovery score. For example, the logic circuits may detect the amount of physical activity and the amount of sleep a user experienced over the last 48 hours, combine those metrics with the user's HRV, and calculate a recovery score of between 1 and 10, wherein the recovery score could indicate the user's physical condition and aptitude for further physical activity that day. The recovery score may also be calculated on a scale of between 1 and 100, or any other scale or range.

Wristband 100 comprises a material 110 configured to encircle a human wrist. In one embodiment, wristband 100 is adjustable. A cavity 120 is notched on the radially inward facing side of the wristband and shaped to substantially the same dimensions as the profile of the electronic capsule. In addition, an aperture 130 is located in the material 110 within cavity 120. The aperture 130 is shaped to substantially the same dimensions as the profile of the finger biosensor 220. The cavity and aperture combination is designed to detachably couple to the electric capsule 200 such that, when the electric capsule 200 is positioned inside cavity 120, the finger biosensor 220 protrudes through the aperture 130. Electronic capsule 200 may further comprise one or more magnets 260 configured to secure capsule 200 to cavity 120. Magnets 260 may be concealed in casing 250. Alternatively, cavity 120 may be configured to conceal magnets 260 when electric capsule 200 detachably couples to the cavity and aperture combination.

Wristband 100 may further comprise a steel strip 140 concealed in material 110 within cavity 120. In this embodiment, when the electronic capsule 200 is positioned within the cavity 120, the one or more magnets 260 are attracted to the steel strip 140 and pull electronic capsule 200 radially outward with respect to the wristband. The force provided by magnets 260 may detachably secure electronic capsule 200 inside cavity 120. In alternative embodiments, the electronic capsule may be positioned inside the wristband cavity and affixed using a form-fit, press-fit, snap-fit, friction-fit, VELCRO, or other temporary adhesion or attachment technology.

FIG. 2 illustrates a perspective view of one embodiment of the disclosed activity monitoring device, in which wristband 100 and electronic capsule 200 are unassembled. FIG. 3 illustrates a cross-sectional view of one embodiment of a fully assembled wristband with removable athletic monitoring device. FIG. 4 illustrates a side view of an electronic capsule 200 according to one embodiment of the disclosure. FIG. 5 illustrates a cross-sectional view of electronic capsule 200. FIG. 6 is a perspective view of two possible variants of the wristband according to some embodiments of the disclosure. Wristbands may be constructed with different dimensions, including different diameters, widths, and thicknesses, in order to accommodate different human wrist sizes and different preferences.

In some embodiments of the disclosure, the electronic capsule may be detachably coupled to a cavity on a shoe and/or a sock. In other embodiments, the electronic capsule may be detachably coupled to sports equipment. For example, the electronic capsule may be detachably coupled to a skateboard, a bicycle, a helmet, a surfboard, a paddle boat, a body board, a hang glider, or other piece of sports equipment. In these embodiments, the electronic capsule may be affixed to the sports equipment using magnets. Alternatively, in other embodiments, the electronic capsule can be affixed using a form-fit, snap-fit, press-fit, friction-fit suction cup, VELCRO, or other technology that would be apparent to one of ordinary skill in the art.

In one embodiment of the disclosure, the electronic capsule may further comprise an optical sensor such as a heart rate sensor or oximeter. In this embodiment, the optical sensor may be positioned to face radially inward towards a human wrist when the wristband is fit on the human wrist. Alternatively, the optical sensor may be separate from the electronic capsule, but still detachably coupled to the wristband and electronically coupled to the circuit boards enclosed in the electronic capsule. Wristband 100 and electronic capsule 200 may operate in conjunction with a system for providing a smart activity score.

FIG. 7A is a flow diagram illustrating an exemplary method for tracking biological age over time. Referring now to FIG. 7A, a method for tracking biological age over time includes receiving one or more user determinable biological age parameters (UDBP) at step 710, receiving one or more system determinable biological age parameters (SMBP) 720, receiving an interval width ($\Delta_i$) and number of intervals (n), and calculating a biological age (BA) for each i between 0 and n. Calculating a biological age may include: (i) calculating a biological age factor ($BF_i$) as a function of each UDBP and each SMBP at step 742, as illustrated by Equation 1; (ii) calculating $BA_i$ as the product of $BF_i$ and a user's actual age at step 744, as illustrated by Equation 2; (iii) calculating a change in biological age between intervals at step 746, as illustrated by Equation 3; (iv) storing $\Delta BA_i$ and $BA_i$ at step 748; and (v) displaying $\Delta BA_i$, $BA_i$, and a biological age trend at step 750, as illustrated by the trend T in Equation 4.

$$BF_i = f(UDBP, SMBP) \tag{1}$$

$$BA_i = Age * BF_i \tag{2}$$

$$\Delta BA_i = BA_i - BA_{i-1} \tag{3}$$

$$T = \{BA_i; 0 \leq i \leq n\} \tag{4}$$

$$UDBP = \Pi UDBP_j \tag{5}$$

$$SMBP = \Pi SMBP_k \tag{6}$$

Referring to Equation 1, UDBP is a product function of factors that may include a user's actual age, gender, ethnicity, eating habits, stress level profile related to job or personal life, marriage profile, height, weight, body fat index, health metrics such as cholesterol level, blood pressure, and medical history, and other factors known to affect longevity of human life. Each factor, $UDBP_j$, may be given a numerical weighting indicating its effect on either extending or reducing average life based on statistical patterns that are well known in the art. Because the $UDBP_j$ are combined in a product function, as illustrated by Equation 5, each $UDBP_j$ with neutral effect on human longevity may have a value equal to 1, each life-extending $UDBP_j$ may have a value greater than 1, and life-reducing $UDBP_j$ may have a value of less than 1. For example, women tend to live longer than men, and therefore, a male $UDBP_j$ would have a value of less than 1 and a female $UDBP_j$ would have a value of greater than 1. Health conditions that are known to dramatically reduce life may have a $UDBP_j$ value of much less than 1. Other factors may have $UDBP_j$ values of less than 1 or more than 1 as scaled by the level that the factor effects human longevity. This data may be readily pulled from publicly available sources. Each $UDBP_j$ may be combined in a product function, as shown in Equation 5, to result in a combined UDBP factor. Some $UDBP_j$ may change over time, such as a user's actual age, marriage profile, stress profile, or health profile. Accordingly, UDBP is not constant across biological age calculation intervals. Other $UDBP_j$ factors may be incorporated into the biological age factor calculation in Equation 1 as would be known to one of ordinary skill in the art.

Still referring to Equation 1, SMBP is a product function of factors that may be measured and/or calculated by the activity monitoring device, or entered by the user. SMBP factors, $SMBP_k$, may include sleep profile, activity profile, recovery scores based on heart rate variability, activity scores, and smart activity scores. Just as with UDBP, because the $SMBP_k$ are combined in a product function, as illustrated in Equation 6, each $SMBP_k$ with neutral effect on human longevity may have a value equal to 1, each life-extending $SMBP_k$ may have a value greater than 1, and each life-reducing $SMBP_k$ may have a value of less than 1. For example, users who do not sleep or activity regularly may have sleep or activity profile each $SMBP_k$ values of less than 1, whereas users with higher activity scores may have activity score $SMBP_k$ values of greater than 1. Further, users with more resilient HRVs may have HRV $SMBP_k$ values of greater than 1, whereas users with less resilient HRVs may have HRV $SMBP_k$ values of less than 1. As discussed, each $SMBP_k$ may be combined in a product function, as illustrated in Equation 6, to generate a combined SMBP factor. Each $SMBP_k$ may change over time depending on changes in measured results from the activity monitoring device or entries from the user. Other $SMBP_k$ may be incorporated into the biological age factor calculation in Equation 1 as would be known to one of ordinary skill in the art.

Still referring to Equation 1, the sleep profile $SMBP_k$ may refer to both the quality and quantity of sleep. For example, the sleep quality metric may represent the percentage of a user's sleep that is uninterrupted, and the sleep quantity metric may represent the user's total hours per day of sleep compared to average hours of sleep per day across a particular population or as compared to recommended hours of sleep. Similarly, the activity profile $SMBP_k$ may refer to both quality and quantity of activity. For example, the activity quality metric may represent the average intensity level of a user's activity, and the activity quantity metric may represent the total hours per day of activity as compared with an average total hours per day of activity across a population or as compared to a recommended total hours of activity. The sleep profile and activity profile $SMBP_k$ may be measured by an activity monitoring device as discussed previously with respect to FIGS. 1 through 6. Similarly, activity score and smart activity score $SMBP_k$ may be measured and calculated by an activity monitoring device as previously discussed with respect to FIGS. 1 through 6.

Referring to Equation 2, UDBP and SMBP may be combined in a single biological age factor ($BF_i$) and multiplied by actual age to generate a biological age ($BA_i$) for any given time interval i. As both UDBP and SMBP values may change over time, the $BF_i$ may also change over time, and consequently, the $BA_i$ may also change over time.

Referring to Equation 3, biological age calculations $BA_i$ from different each time interval i may be compared with the biological age calculation $BA_{i-1}$ from the immediately preceding time interval (i−1) to generate a $\Delta BA_i$.

Referring to Equation 4, a biological age trend function y(BA) may plot each $BA_i$ against each i from an initial time interval i=0 to a current time interval i=n.

Figure 7B:
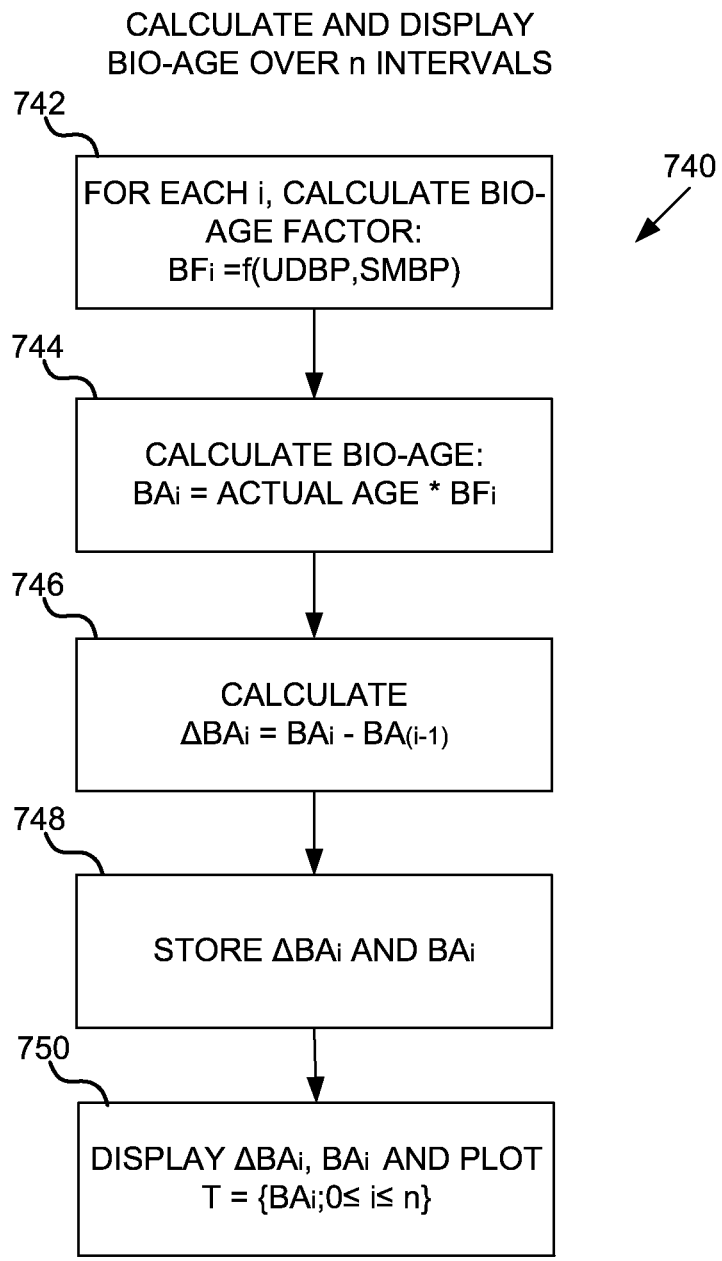
FIG. 7B is a flow diagram illustrating an exemplary method of calculating and displaying biological age over multiple time intervals.

FIG. 7B is a flow diagram illustrating an exemplary method of calculating and displaying biological age over multiple time intervals. Referring now to FIG. 7B, a method for calculating and displaying biological age over multiple time intervals includes calculating a biological age factor BAi as per Equation 1 at step 742, calculating a biological age BAi as per Equation 2 at step 744, calculating a $\Delta BA_i$ as per Equation 3 at step 746, storing the BAi and $\Delta BA_i$ at step 748, and displaying $BA_i$, $\Delta BA_i$, and a plot of a biological age trend function T as per Equation 4 at step 750. The displaying at step 750 may be performed by a mobile device, a computer, or other computing devices as may be known in the art.

In some embodiments, a method for tracking and displaying biological age may include calculating and displaying recommendations to the user. Some of these embodiments may include systems and methods for comparing biological age with physical activity monitoring, calculating recommended activity regiments to reduce, maintain, or achieve a desired biological age, and monitoring progress towards achieving the desired biological age. For example, the user may determine a target biological age and adjust specific $UDBP_j$ and/or $SMBP_k$ to achieve that target. Alternatively, one embodiment may include calculating adjustments to $UDBP_j$ and/or $SMBP_k$ required to match the user's biological age to the user's actual age. In order to decrease biological age, the user may be required to increase sleep and/or activity quantity or quality, eat healthier, or find ways to lower stress. These adjustments may be monitored and progress tracked by displaying the biological age trend function plot as described in Equation 4 and at step 750.

In some examples, a system and method for tracking biological age over time may also displays physical activity trends over time, and may additionally flag changes in biological age on a correlated or combined display with physical activity trend changes such that a user may determine what physical activity characteristics may have caused the change in biological age. In one example, the system may also analyze the correlation between changes in biological age and lifestyle (e.g. physical activity, sleep patterns, eating habits, etc.) by using historical or known data trends to predict display advise indicating what lifestyle conditions may have affected the biological age change(s). In this example, a lifestyle trend may be displayed in a temporally synchronous display with a biological age trend. Here, temporally synchronous means that the lifestyle trend and biological age trend share the same temporal axis such that corresponding points on the lifestyle trend and biological trend are each derived from data collected at the same time. The system may further analyze, predict, and display advice indicating possible lifestyle changes would be necessary to return the biological age to a target value.

Figure 8A:
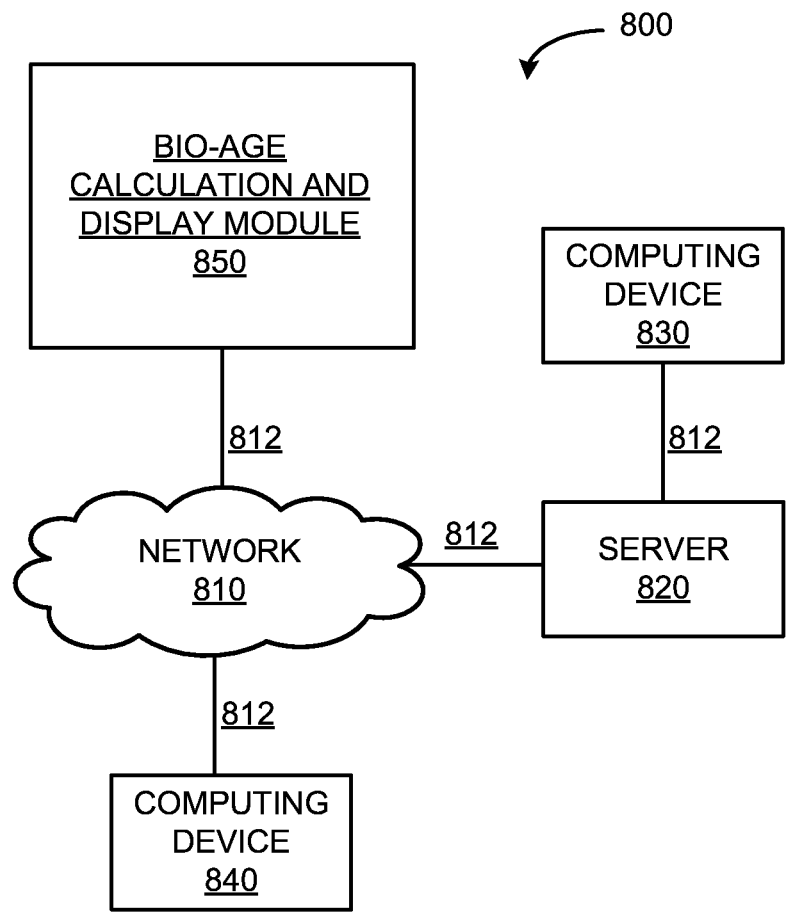
FIG. 8A illustrates a system for communicating biological age data between system modules.

FIG. 8A is a schematic block diagram illustrating one embodiment of a system for communicating biological age data between system modules. System 800 includes multiple devices for communicating, calculating, and displaying biological age. For example, biological age calculation and display module 850 may connect to network 810 via communications mechanisms 812, 814, 816, and 818. The communications mechanisms may include various known technologies, including WAN, LAN, Wi-FI, TCP/IP, Bluetooth®, 4G LTE, or other known communications standards. The system for communicating metrics of interest may also include server 820 and computing devices 830 and 840.

Communication network 810 may be implemented in a variety of forms. For example, communication network 810 may be an Internet connection, such as a local area network ("LAN"), a wide area network ("WAN"), a fiber optic network, internet over power lines, a hard-wired connection (e.g., a bus), and the like, or any other kind of network connection. Communication network 804 may be implemented using any combination of routers, cables, modems, switches, fiber optics, wires, radio, and the like and using various wireless standards, such as Bluetooth®, Wi-FI, or 4G LTE such as to be compatible with the communications mechanisms. One of skill in the art will recognize other ways to implement communication network 810.

Server 820 may direct communications made over communications network 810. Server 820 may be, for example, an Internet server, a router, a desktop or laptop computer, a smartphone, a tablet, a processor, a module, or the like. In one embodiment, server 820 directs communications between communications network 810 and computing devices 830 and/or 840. For example, server 820 may update information stored on computing device 830, or server 820 may send information to computing device 840 in real time.

Computing device 840 may take a variety of forms, such as a desktop or laptop computer, a smartphone, a tablet, a processor, or a module. In addition, computing device 840 may be a processor or module embedded in a wearable sensor, a bracelet, a smart-watch, a piece of clothing, an accessory, and so on. For example, computing device 840 may be substantially similar to devices embedded in electronic capsule 200, which may be embedded in and removable from wristband 100, as illustrated in FIG. 1. Computing device 840 may communicate with other devices over communication medium 810 with or without the use of server 820. In one embodiment, computing device 840 includes electronic capsule 200.

Figure 8B:
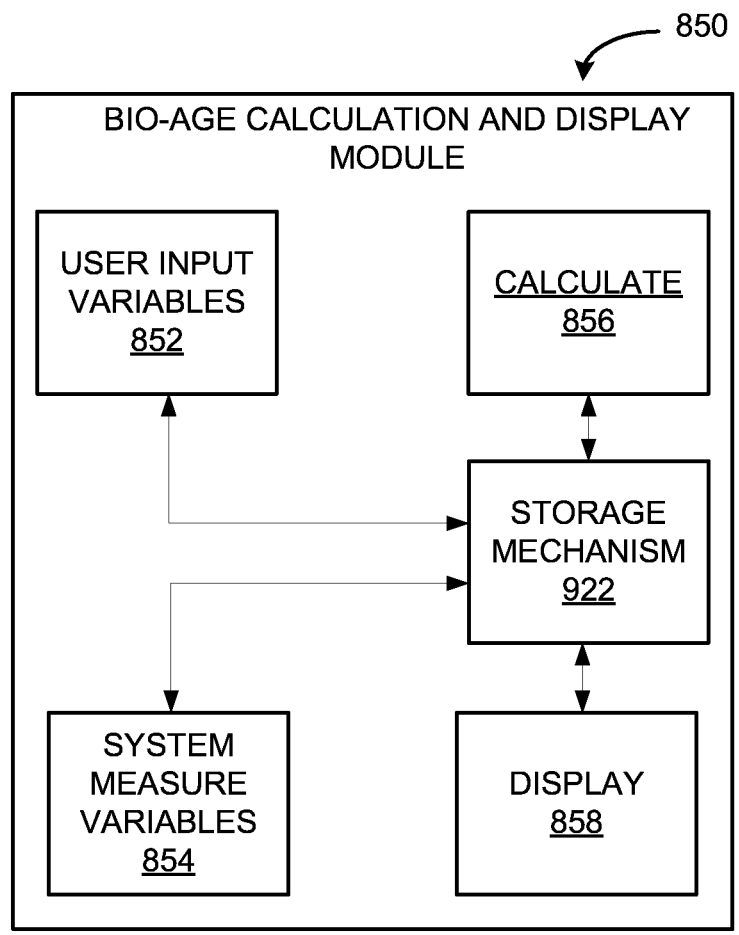
FIG. 8B illustrates a biological age calculation and display module.

FIG. 8B is a schematic block diagram illustrating a biological age calculation and display module. Referring now to FIG. 8B, a biological age calculation and display module 850 may comprise user determinable biological factor (UDBP) receiving module 852, system measurable biological factor (SMBP) receiving module 854, biological factor (BF) calculation module 856, display module 858, and storage mechanism 922. The UDBP receiving module 852 may be configured to receive input of $UDBP_j$ from users. User input into the UDBP module may be stored in storage mechanism 922. The SMBP receiving module 854 may be configured to receive input of $SMBP_k$ from users or from an activity monitoring device. For example, referring again to FIG. 1, electronic capsule 200 may detect and calculate $SMBP_k$ and transmit them to SMBP receiving module 854. User input into the SMBP receiving module may be stored in storage mechanism 922. BF calculation module 856 may receive $UDBP_j$ and $SMBP_k$ from storage mechanism 922 and calculate biological age factors, biological age, biological age changes over time, and a biological age trend function as shown in Equation 4. Display module 858 may be configured to display biological age, changes in biological age, and a biological age trend plot.

Figure 9:
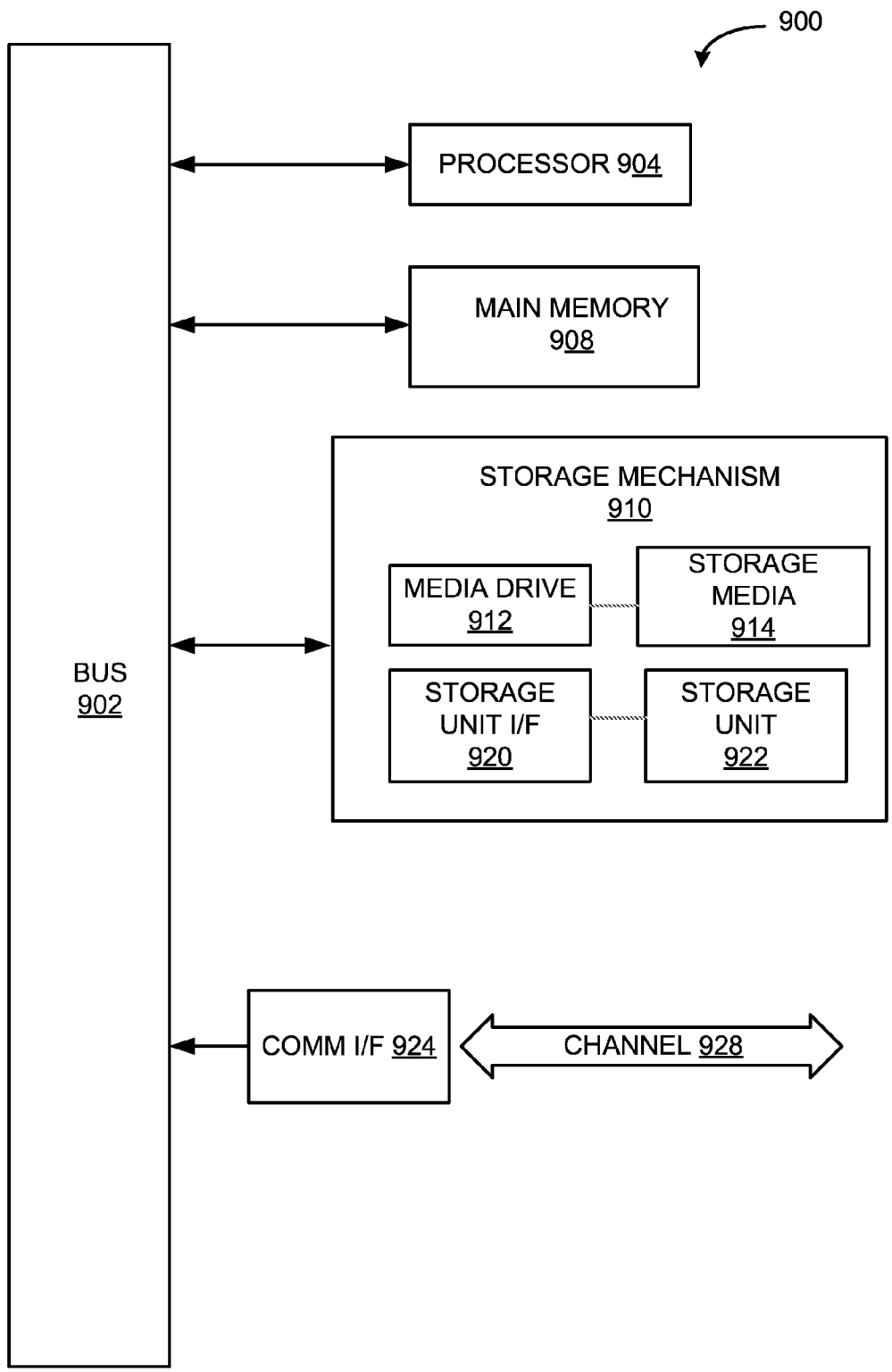
FIG. 9 illustrates an example computing module that may be used to implement various features of the systems and methods disclosed herein.

FIG. 9 illustrates an example computing module that may be used to implement various features of the systems and methods disclosed herein. In one embodiment, the computing module includes a processor and a set of computer programs residing on the processor. The set of computer programs may be stored on a non-transitory computer readable medium having computer executable program code embodied thereon. The computer executable code may be configured to monitor a movement to determine a metabolic loading associated with the movement. The computer executable code may be configured to create and update a metabolic activity score based on the metabolic loading. The computer executable code may be configured to detect a fatigue level. The computer executable code may be configured to create and update a smart activity score by modifying the activity score based on the fatigue level.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 9. Various embodiments are described in terms of this example-computing module 900. After reading this description, it will become apparent to a person skilled in the relevant art how to implement the application using other computing modules or architectures.

Referring now to FIG. 9, computing module 900 may represent, for example, computing or processing capabilities found within desktop, laptop, notebook, and tablet computers; hand-held computing devices (tablets, PDA's, smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing module 900 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 900 might include, for example, one or more processors, controllers, control modules, or other processing devices, such as a processor 904. Processor 904 might be implemented using a general-purpose or special-purpose processing engine such as, for example, a microprocessor, controller, or other control logic. In the illustrated example, processor 904 is connected to a bus 902, although any communication medium can be used to facilitate interaction with other components of computing module 900 or to communicate externally.

Computing module 900 might also include one or more memory modules, simply referred to herein as main memory 908. For example, preferably random access memory (RAM) or other dynamic memory, might be used for storing information and instructions to be executed by processor 904. Main memory 908 might also be used for storing temporary variables or other intermediate information during execution of instructions to be executed by processor 904. Computing module 900 might likewise include a read only memory ("ROM") or other static storage device coupled to bus 902 for storing static information and instructions for processor 904.

The computing module 900 might also include one or more various forms of information storage mechanism 910, which might include, for example, a media drive 912 and a storage unit interface 920. The media drive 912 might include a drive or other mechanism to support fixed or removable storage media 914. For example, a hard disk drive, a solid state drive, a magnetic tape drive, an optical disk drive, a CD or DVD drive (R or RW), or other removable or fixed media drive might be provided. Accordingly, storage media 914 might include, for example, a hard disk, a solid state drive, magnetic tape, cartridge, optical disk, a CD or DVD, or other fixed or removable medium that is read by, written to or accessed by media drive 912. As these examples illustrate, the storage media 914 can include a computer usable storage medium having stored therein computer software or data.

In alternative embodiments, information storage mechanism 910 might include other similar instrumentalities for allowing computer programs or other instructions or data to be loaded into computing module 900. Such instrumentalities might include, for example, a fixed or removable storage unit 922 and a storage interface 920. Examples of such storage units 922 and storage interfaces 920 can include a program cartridge and cartridge interface, a removable memory (for example, a flash memory or other removable memory module) and memory slot, a PCMCIA slot and card, and other fixed or removable storage units 922 and storage interfaces 920 that allow software and data to be transferred from the storage unit 922 to computing module 900.

Computing module 900 might also include a communications interface 924. Communications interface 924 might be used to allow software and data to be transferred between computing module 900 and external devices. Examples of communications interface 924 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 924 might typically be carried on signals, which can be electronic, electromagnetic (which includes optical) or other signals capable of being exchanged by a given communications interface 924. These signals might be provided to communications interface 924 via a channel 928. This channel 928 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 908, storage unit 920, media 914, and channel 928. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing module 900 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. A computer implemented method comprising executing by a computing module, which comprises a processor, the steps of:
   receiving, by the computing module, one or more user determinable biological age parameters including an actual age;
   receiving, by the computing module, one or more system measurable biological age parameters from an activity monitoring device, wherein the activity monitoring device comprises a biosensor, and wherein the system measurable biological age parameters comprise:
      a measure of the user's heart rate variability;
      an amount of physical activity performed by the user within a period of time; and
      a sleep profile for the user, wherein the sleep profile comprises:
         an average sleep quality metric, wherein the average sleep quality metric represents an average percentage of the user's sleep that is uninterrupted; and
         an average sleep quantity metric, wherein the average sleep quantity metric represents an average quantity of sleep within a period of time;
   calculating, by the computing module, a biological age factor as a function of the user determinable biological age parameters and the system measurable biological age parameters;
   calculating, by the computing module, biological age as a function of the biological age factor and the actual age;
   displaying the biological age;
   calculating, by the computing module, a recovery score based on the system measurable biological age parameters; and
   displaying the recovery score, wherein the recovery score provides a recommendation for the user's physical activity that is to occur in the future.

2. The method of claim 1, further comprising:
   receiving a time interval width and desired number of time intervals for which to track biological age;

calculating, for each time interval, a corresponding interval specific biological age;

storing, for each time interval, the corresponding interval specific biological age;

creating a biological age trend graph in which time intervals are plotted on an x-axis and corresponding interval specific biological ages are plotted on a y-axis; and displaying the biological age trend graph.

3. The method of claim 1, wherein the system measurable biological age parameters further comprise an activity profile, an activity score, and a smart activity score.

4. The method of claim 3, further comprising displaying a lifestyle trend graph temporally synchronous with the biological age trend graph, wherein the lifestyle trend graph comprises the activity profile.

5. The method of claim 4, further comprising:
calculating a correlation between changes in the lifestyle trend graph and changes in the biological age trend graph;
comparing the correlation to a threshold; and
if the correlation exceeds the threshold, generating an alert flag indicating that the threshold has been exceeded and displaying the alert flag.

6. The method of claim 3, further comprising:
measuring and calculating, by the activity monitoring device, at least one of the system measurable activity parameters, wherein the activity profile comprises an average activity quality metric and an average activity quantity metric.

7. The method of claim 1, wherein the user determinable biological age parameters further comprise gender, ethnicity, eating habits, stress level, marriage profile, height, weight, body fat index, cholesterol level, blood pressure, and medical history.

8. The method of claim 7, further comprising:
determining one or more adjustments to the system measurable biological age parameters and the user determinable biological age parameters, if achieved, will render the biological age equal to the actual age.

9. The method of claim 1, further comprising receiving a target biological age and displaying the target biological age.

10. The method of claim 9, further comprising:
determining one or more adjustments to the system measurable biological age parameters and the user determinable biological age parameters that, if achieved, will render the biological age equal to the target biological age.

11. A system for tracking biological age comprising:
an activity monitoring device, wherein the activity monitoring device comprises a biosensor; and
a biological age calculation and display module;
wherein the activity monitoring device is configured to:
measure one or more system measurable biological age parameters using the biosensor, wherein the system measurable biological age parameters comprise:
a measure of the user's heart rate variability;
an amount of physical activity performed by the user within a period of time; and
a sleep profile for the user, wherein the sleep profile comprises:
an average sleep quality metric, wherein the average sleep quality metric represents an average percentage of the user's sleep that is uninterrupted; and
an average sleep quantity metric, wherein the average sleep quantity metric represents an average quantity of sleep within a period of time; and
transmit the system measurable biological age parameters to the biological age calculation and display module, and
wherein the biological age calculation and display module is configured to:
(i) receive the system measurable biological age parameters;
(ii) receive user determinable biological age parameters including an actual age from a user;
(iii) calculate a biological age factor as a function of the user determinable biological age parameters and the system measurable biological age parameters;
(iv) calculate biological age as a function of the biological age factor and the actual age;
(v) display the biological age;
(vi) calculate a recovery score based on the system measurable biological age parameters; and
(vii) display the recovery score, wherein the recovery score provides a recommendation for the user's physical activity that is to occur in the future.

12. The system of claim 11, wherein the biological age calculation and display module comprises one or more biological age parameter receiving modules, a biological age calculation module, a display module, and a storage medium, wherein
the biological age parameter receiving modules are configured to store on the storage medium the system measurable biological age parameters and the user determinable biological age parameters including a time interval width and desired number of time intervals for which to track biological age;
the biological age calculation module is configured to read from the storage medium the system determinable biological age parameters and the user determinable biological age parameters, and calculate and store on the storage medium an interval specific biological age for each time interval and a biological age trend graph, wherein the biological age trend graph comprises time intervals plotted on an x-axis and corresponding interval specific biological ages on a y-axis; and
the display module is configured to read from the storage medium and display the biological age trend graph.

13. The system of claim 12, wherein one of the biological age parameter receiving modules is further configured to receive a target biological age and wherein the display module is further configured to display the target biological age.

14. The system of claim 13, wherein the biological age calculation module is further configured to determine one or more adjustments to the system measurable biological age parameters and user determinable biological age parameters that, if achieved, will render the biological age equal to the target biological age.

15. The system of claim 11, further comprising one or more computing devices and a communications network, wherein the biological age calculation and display module receives user determinable biological age parameters through the communications network from at least one of the computing devices.

16. The system of claim 11, wherein the user determinable biological age parameters further comprise gender, ethnicity, eating habits, stress level, marriage profile, height, weight, body fat index, cholesterol level, blood pressure, and medical history.

17. The system of claim 11, wherein the biological age calculation and display module is further configured to determine one or more adjustments to the system measurable biological age parameters and the user determinable biological age parameters that, if achieved, will render the biological age equal to the actual age.

18. The system of claim 11, wherein the system measurable biological age parameters further comprise an activity profile, an activity score, and a smart activity score.

19. The system of claim 18, wherein the display module is further configured to display a lifestyle trend function temporally synchronous with the biological age trend function, and wherein lifestyle trend function comprises the activity profile.

20. The system of claim 19, wherein the biological age calculation module is further configured to calculate a correlation between changes in the lifestyle trend graph and changes in the biological age trend graph, compare the correlation to a threshold, and, if the correlation exceeds the threshold, generate an alert flag indicating that the threshold has been exceeded, and wherein the display module is further configured to display the alert flag.

21. The system of claim 18, wherein the activity profile comprises an average activity quality metric and an average activity quantity metric.

22. A system for tracking biological age comprising:
an activity monitoring device, wherein the activity monitoring device comprises a biosensor and one or more logic circuits; and
a biological age calculation and display module;
wherein the activity monitoring device is configured to measure one or more system measurable biological age parameters and transmit the system measurable biological age parameters to the biological age calculation and display module, wherein the activity monitoring device is further configured to calculate a recovery score based on the system measurable biological age parameters, wherein the system measurable biological age parameters comprise:
a measure of the user's heart rate variability;
an amount of physical activity performed by the user within a period of time; and
a sleep profile for the user, wherein the sleep profile comprises:
an average sleep quality metric, wherein the average sleep quality metric represents an average percentage of the user's sleep that is uninterrupted; and
an average sleep quantity metric, wherein the average sleep quantity metric represents an average quantity of sleep within a period of time, and
wherein the biological age calculation and display module comprises one or more biological age parameter receiving modules, a biological age calculation module, a display module, and a storage medium, and
wherein:
the biological age parameter receiving modules are configured to store on the storage medium one or more biological age parameters;
the biological age calculation module is configured to read from the storage medium the biological age parameters, calculate a biological age factor as a function of the biological age parameters, calculate a biological age as a function of actual age and the biological age factor, and store on the storage medium the biological age;
the display module is configured to read from the storage medium and display the biological age; and
the display module is further configured to display the recovery score, wherein the recovery score provides a recommendation for the user's physical activity that is to occur in the future.

* * * * *